(12) United States Patent
Sentell

(10) Patent No.: US 11,786,351 B2
(45) Date of Patent: Oct. 17, 2023

(54) DOUBLE CLAMPING SURGICAL TOWEL CLAMP

(71) Applicant: Rex Sentell, Stuart, FL (US)

(72) Inventor: Rex Sentell, Stuart, FL (US)

( * ) Notice: Subject to any disclaimer, the term of this patent is extended or adjusted under 35 U.S.C. 154(b) by 185 days.

(21) Appl. No.: 17/488,910

(22) Filed: Sep. 29, 2021

(65) Prior Publication Data

US 2023/0102180 A1  Mar. 30, 2023

(51) Int. Cl.
*A61B 17/28* (2006.01)
*A61B 17/00* (2006.01)
*A61D 1/00* (2006.01)
*A61B 46/00* (2016.01)

(52) U.S. Cl.
CPC .............. *A61D 1/00* (2013.01); *A61B 17/28* (2013.01); *A61B 17/2833* (2013.01); *A61B 46/00* (2016.02); *A61B 2017/0042* (2013.01); *A61B 2017/2808* (2013.01); *A61B 2017/2837* (2013.01)

(58) Field of Classification Search
CPC .............. A61B 17/28; A61B 17/2833; A61B 2017/2808; A61B 2017/2837; A61B 17/2804; A61B 17/282; A61B 17/2841; A61B 2017/0042; A61B 17/29; A61B 2017/00353; A61B 2017/00473; A61B 17/062; A61B 17/30; A61B 17/3201; A61B 2017/303; A61B 17/2812; A61B 17/2816; A61B 46/00; A61D 1/00; B25F 1/00; B25F 1/003; B25F 1/006; B25F 1/02; B25F 1/04; B26B 13/22; B26B 13/00; B25B 7/00; B25B 7/02; B25B 7/22
USPC ........................................................... 30/341
See application file for complete search history.

(56) References Cited

U.S. PATENT DOCUMENTS

| | | | |
|---|---|---|---|
| 2,422,207 A * | 6/1947 | Nalpantian | A45D 29/02 30/28 |
| 3,646,939 A | 3/1972 | Sklar | |
| 4,024,870 A | 5/1977 | Sandel | |
| 4,611,592 A | 9/1986 | Talboy | |
| 9,522,001 B2 | 12/2016 | Bui et al. | |
| 2005/0283981 A1* | 12/2005 | Yizhar | B26B 13/22 30/142 |
| 2012/0101518 A1 | 4/2012 | DePond | |

* cited by examiner

*Primary Examiner* — Brooke Labranche
*Assistant Examiner* — Lauren Dubose
(74) *Attorney, Agent, or Firm* — Mark Terry

(57) ABSTRACT

A surgical towel clamp apparatus includes a first elongated element having a curved tip and a right finger ring, a second elongated element having a curved tip and a left finger ring, wherein the first and second elongated elements are coupled at a first pivot point, a third elongated element having a straight tip and coupled to the right finger ring, a fourth elongated element having a straight tip and coupled to the left finger ring, wherein the third and fourth elongated elements are coupled at a second pivot point, wherein in an open orientation, the rings are apart, the curved tips are apart, and the straight tips are apart, and wherein in a closed orientation, the left and right finger rings are adjacent, the curved tips are in contact and the straight tips are in contact.

12 Claims, 5 Drawing Sheets

DOUBLE CLAMPING SURGICAL TOWEL CLAMP

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention disclosed broadly relates to the field of medical devices, and more particularly relates to the field of surgical devices for facilitating the surgical process.

BACKGROUND OF THE INVENTION

Veterinary surgical operations require the use of proper tools to ensure the safety of the animals being operated on. Towel clamps are common surgical tools used to affix a towel or surgical drape onto a surgical area, such as by affixing the towel or surgical drape onto the skin of the animal being operated on. The current towel clamps come with several defects that may detract from the safety and effectiveness of the operation. Among these defects is the difficulty that comes with using said clamps on animals. When attempting to secure cloth to an animal, the towel clamps currently in use may become loosened as the skin recedes into its original position, requiring the constant monitoring and adjustment of surgical staff. Also, it is common that loops of suture material catch on the towel clamp between the fingered holds 107, 108 for the towel clamp, which happens frequently when suturing.

The constant monitoring and adjustment required by surgical staff to ensure the safety of the animal being operated on while using towel clamps detracts from the time and attention at their disposal to ensure a successful operation. Should surgical staff commit an error during an operation due to having been distracted by constantly monitoring and adjusting towel clamps and sutures, said professionals may face significant cost and liability. From an ethical standpoint, it is most commendable to put the safety and well-being of the animal in veterinary care at the forefront. This is made more difficult when using towel clamps on animals during suturing, where the constant monitoring and adjusting of the clamps and sutures adds an unnecessary step to already complex operations.

From a practical standpoint, should surgical staff complete an operation more quickly while preserving safety and effectiveness, they may operate on more animals in less time, resulting in improved business prospects. Because of the aforementioned defects, it becomes necessary to improve upon the prior art. Therefore, a need exists to overcome the problems with the prior art as discussed above, and particularly for a more effective and efficient surgical towel clamp.

SUMMARY OF THE INVENTION

Briefly, according to one embodiment, a surgical towel clamp apparatus includes a first elongated element having a curved tip at a distal end, and a right finger ring at a proximal end; a second elongated element having a curved tip at a distal end, and a left finger ring at a proximal end, wherein the first and second elongated elements are coupled at a first pivot point located between the distal and proximal ends of the first and second elongated elements; a third elongated element having a straight tip at a distal end, and coupled to the right finger ring at a proximal end; a fourth elongated element having a straight tip at a distal end, and coupled to the left finger ring at a proximal end, wherein the third and fourth elongated elements are coupled at a second pivot point located between the distal and proximal ends of the third and fourth elongated elements; wherein in an open orientation, the left and right finger rings are apart, the curved tip of the first elongated element is apart from the curved tip of the second elongated element; and the straight tip of the third elongated element is apart from the straight tip of the fourth elongated element; and wherein in a closed orientation, the left and right finger rings are adjacent, the curved tip of the first elongated element contacts the curved tip of the second elongated element; and the straight tip of the third elongated element contacts the straight tip of the fourth elongated element.

The foregoing and other features and advantages of the present invention will be apparent from the following more particular description of the preferred embodiments of the invention, as illustrated in the accompanying drawings.

BRIEF DESCRIPTION OF THE DRAWINGS

The accompanying drawings, which are incorporated in and constitute a part of this disclosure, illustrate various example embodiments. In the drawings.

DETAILED DESCRIPTION

Figure 1A:
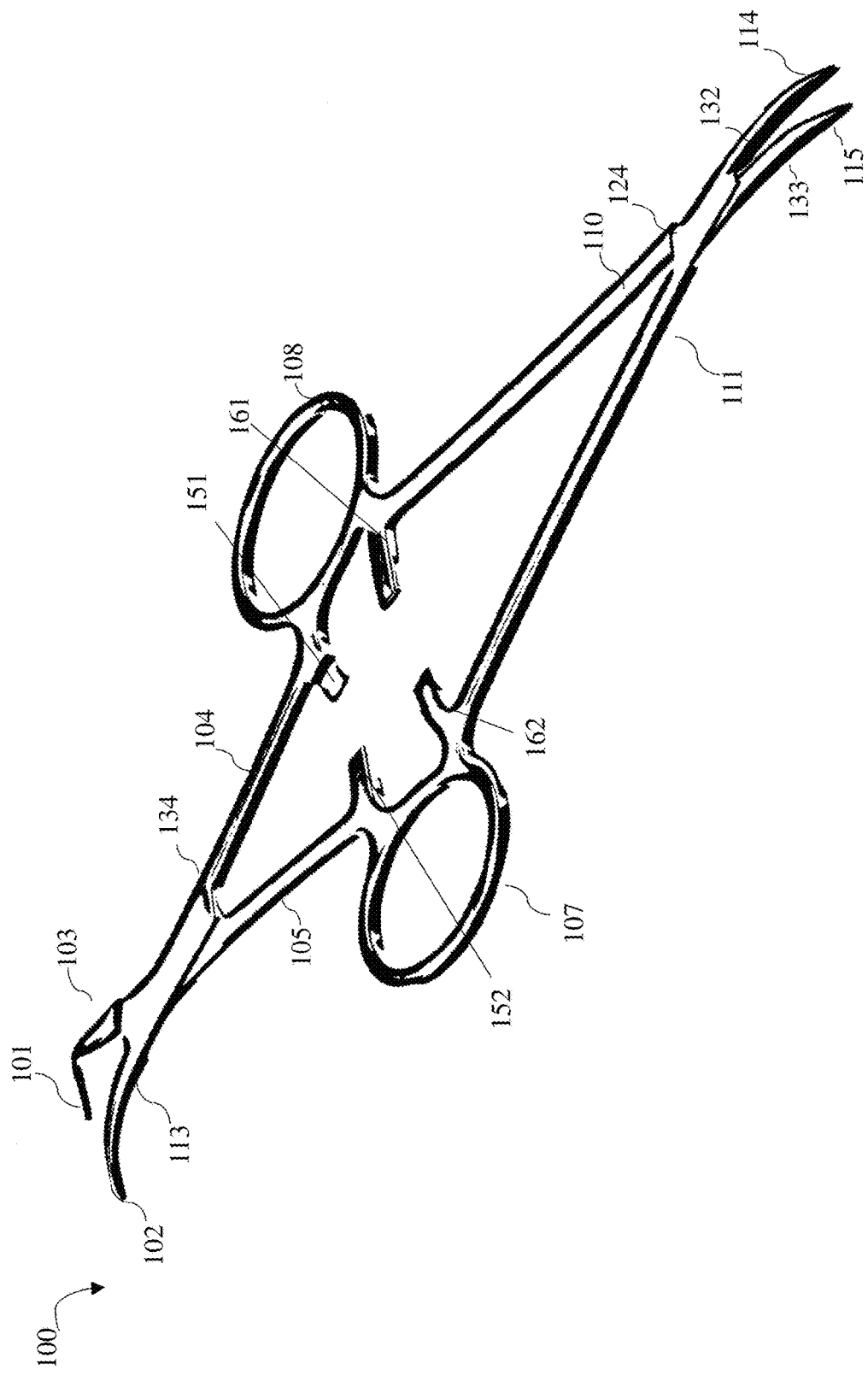
FIG. 1A is a top perspective view of a surgical towel clamp in open orientation, in accordance with one embodiment.

The following detailed description refers to the accompanying drawings. Wherever possible, the same reference numbers are used in the drawings and the following description to refer to the same or similar elements. While embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the claimed subject matter. Instead, the proper scope of the claimed subject matter is defined by the appended claims.

The claimed subject matter improves over the prior art by providing an improved surgical towel clamp that is more efficient and easier to utilize than prior art towel clamps. Applicant's claimed embodiments further address problems with the prior art towel clamps by implementing a second clamp that secures itself to the surgical cloth, preventing the receding of taut skin when the surgeon clamps a bight of skin to facilitate access to internal organs. From an ethical standpoint, a second clamp ensures a safer, more effective operation by eliminating a distraction that detracts from the time surgical staff spend on the animal's illness or injury. From a practical standpoint, a second clamp, by eliminating distractions, ensures the operation is completed in a more time-effective manner, ensuring surgical staff can treat more animals in the same amount of time. Additionally, the claimed embodiments prevent loops of suture material from catching on the towel clamp between the fingered holds, which happens frequently when suturing. With the additional clamp to clamp the surgical towel or drape, the suture material will slide over the towel clamp and will not get caught in the towel clamp. That is, the structure of the claimed towel clamp does not allow a length of suture to enter between the fingered holds of the towel clamp, as in a flossing action. This claimed feature speeds up the surgery and shortens the anesthesia time, which results in better surgical outcomes.

Figure 1B:
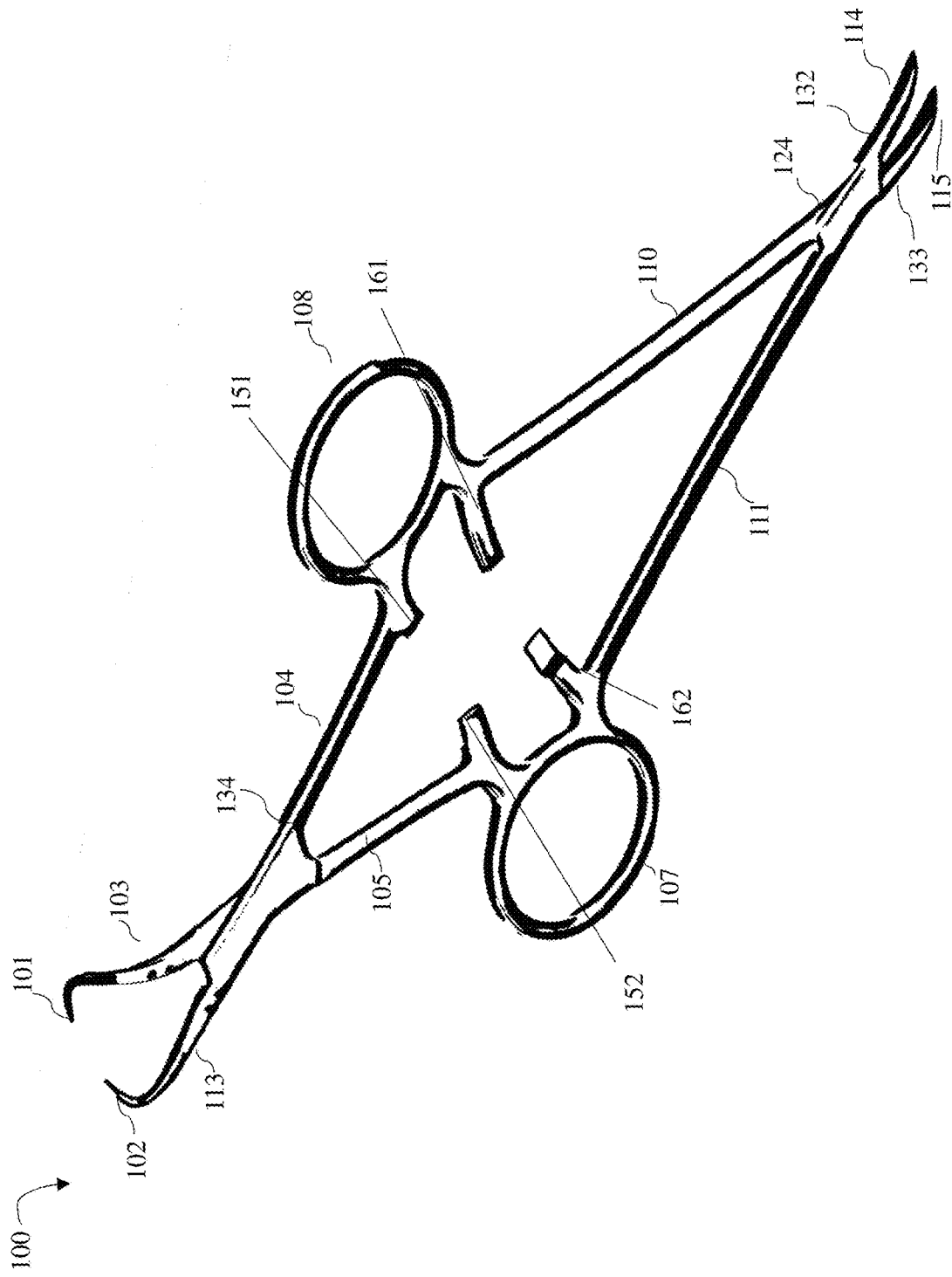
FIG. 1B is another top perspective view of the surgical towel clamp in open orientation, in accordance with one embodiment.
Figure 2A:
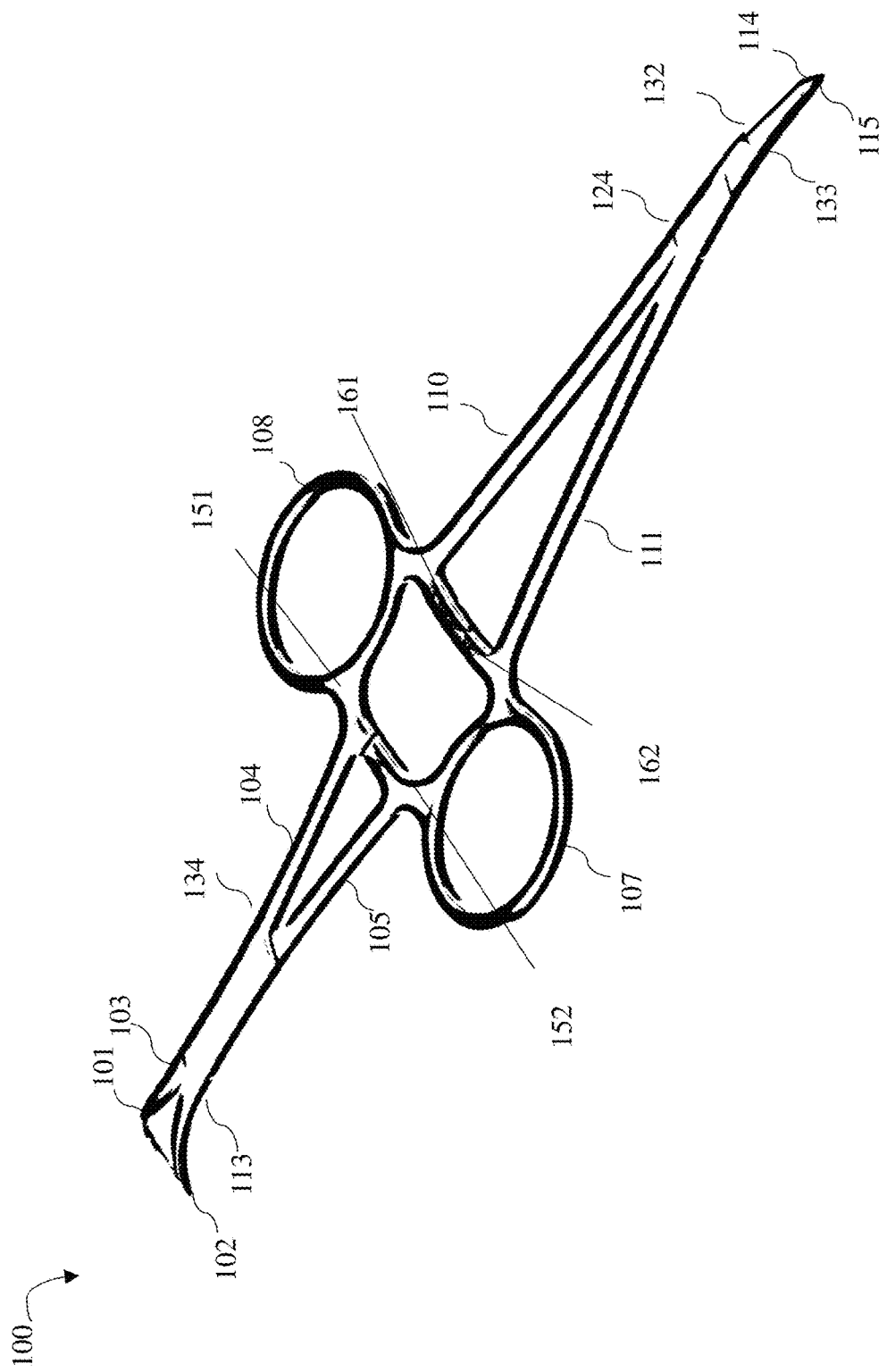
FIG. 2A is a top perspective view of the surgical towel clamp in closed orientation, in accordance with one embodiment.
Figure 2B:
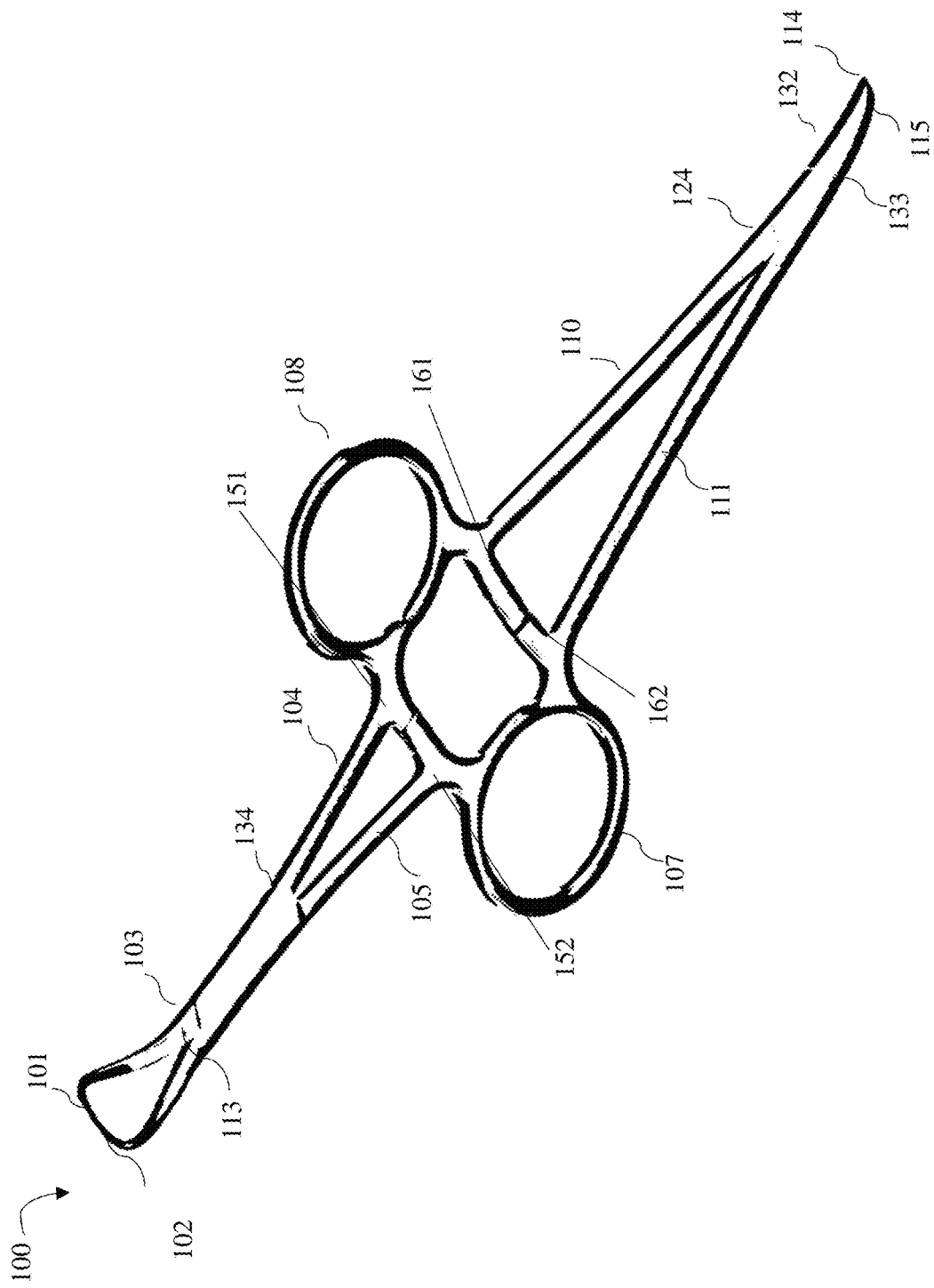
FIG. 2B is another top perspective view of the surgical towel clamp in closed orientation, in accordance with one embodiment.
Figure 3:
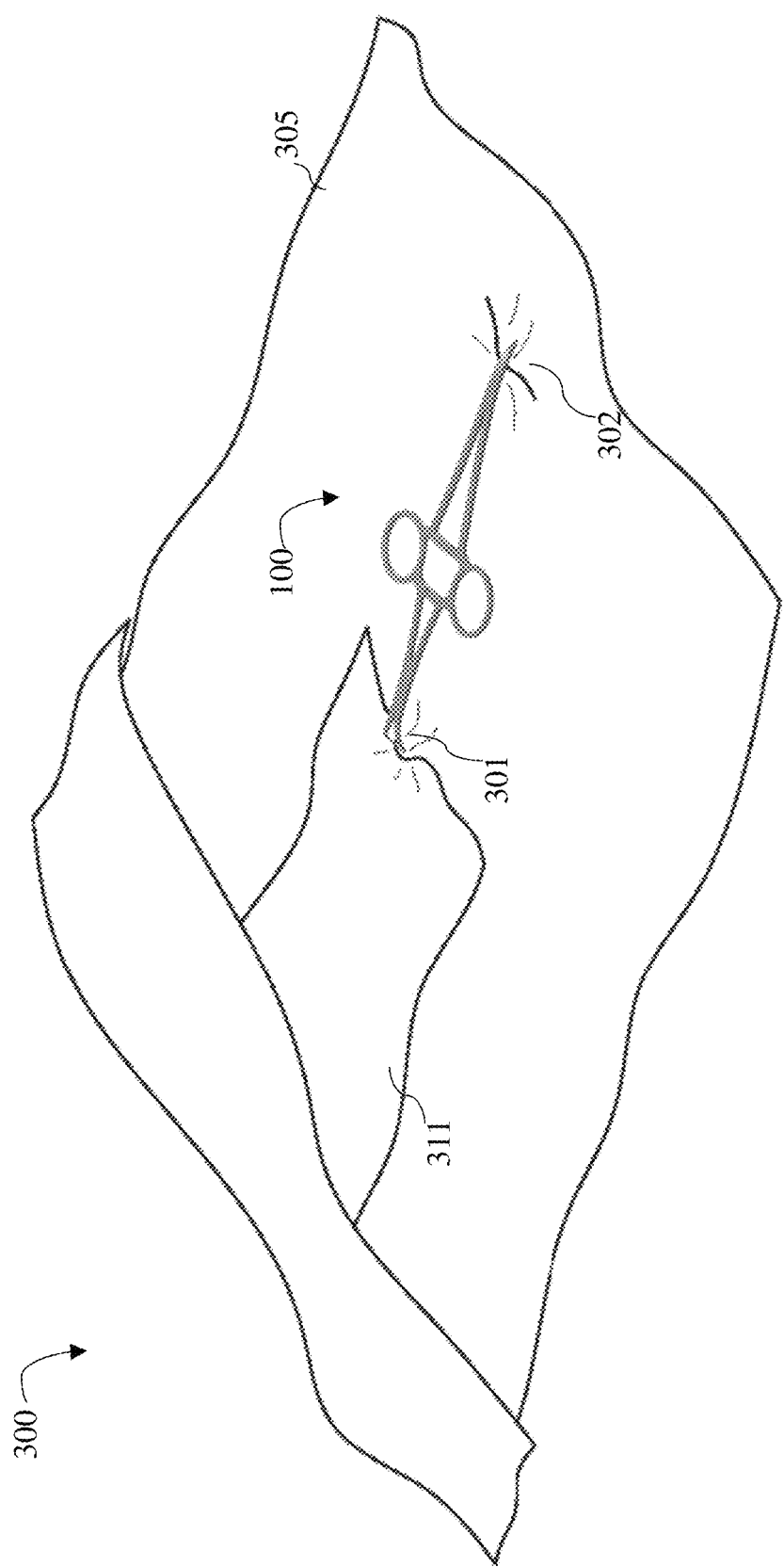
FIG. 3 is a perspective view of the surgical towel clamp in use during an operation, in accordance with one embodiment.

The claimed subject matter will now be described with reference to the FIGS. 1A-3. FIGS. 1A-1B are perspective views of a surgical towel clamp 100 in open orientation, while FIGS. 2A-2B are perspective views of the surgical towel clamp 100 in closed orientation, in accordance with one embodiment. FIG. 3 is a perspective view of the surgical towel clamp 100 in use during an operation, in accordance with one embodiment.

FIGS. 1A-1B are perspective views of a surgical towel clamp 100 in open orientation, in accordance with one embodiment. The towel clamp 100 consists of two separate clamps that are meant to be secured onto a surgical cloth to secure a surgical area for operation. The towel clamp 100 may be used to secure open one more surgical towels and/or surgical incisions, so as to facilitate the surgeon's performing of the operation.

FIGS. 1A-1B show that the surgical towel clamp 100 includes a first elongated element (or clamp leg) 104 having a curved tip 102 at a distal end, and a right finger (or thumb) ring 108 at a proximal end, as well as a second elongated element (or clamp leg) 105 having a curved tip 101 at a distal end, and a left finger (or thumb) ring 107 at a proximal end. The first and second elongated elements 104, 105 are coupled at a first pivot point 134 located between the distal and proximal ends of the first and second elongated elements. The curved tips 101, 102 of the first and second elongated elements point in a first direction (upwards in in the figures).

FIGS. 1A-1B also show that the surgical towel clamp 100 includes a third elongated element 110 having a straight tip 115 at a distal end and coupled to the right finger ring 108 at a proximal end, as well as a fourth elongated element 111 having a straight tip 114 at a distal end and coupled to the left finger ring 107 at a proximal end. The third and fourth elongated elements 110, 111 are coupled at a second pivot point 124 located between the distal and proximal ends of the third and fourth elongated elements. The straight tips 114, 115 of the third and fourth elongated elements point in a second direction opposite the first direction (downwards in the figures).

Since a first clamp (tips 101, 102) is located on a first end of the surgical towel clamp 100 and a second clamp (tips 114, 115) is located on a second end of the surgical towel clamp 100, the surgical towel clamp 100 may be referred to as a double clamped surgical towel clamp.

FIGS. 1A-1B show that in an open orientation, the left and right finger rings 107, 108 are apart, the curved tips 101, 102 of the first and second elongated elements 105, 104 are apart and the straight tips 114, 115 of the third and fourth elongated elements 110, 111 are apart. In use, the user inserts his fingers into the left and right finger rings 107, 108 to pull the rings apart, which results in the curved tips 101, 102 of the first and second elongated elements 105, 104 being separated and the straight tips 114, 115 of the third and fourth elongated elements 110, 111 being separated, which is the open orientation.

FIGS. 2A-2B are perspective views of the surgical towel clamp 100 in closed orientation, in accordance with one embodiment. FIGS. 2A-2B show that in a closed orientation, the curved distal tip 101 contacts the curved distal tip 102 to secure the clamp onto a surgical cloth and or a bight of skin. FIGS. 2A-2B show that in a closed orientation, the straight distal tip 114 contacts the straight distal tip 115 to secure the clamp onto a surgical cloth and or a bight of skin.

The first hinge or pivot point 134 is located approximately at a midpoint of first elongated element (or clamp leg) 104 and at a midpoint of second elongated element (or clamp leg) 105. The second hinge or pivot point 124 is located approximately at a midpoint of third elongated element (or clamp leg) 110 and at a midpoint of fourth elongated element (or clamp leg) 111.

Left finger ring 107, with a circular or oval shape, provides a place of insertion of the user's digital appendage to open and close the device. Right finger ring 108, with a circular or oval shape, also provides a place of insertion of the user's digital appendage to open and close the device.

FIGS. 2A-2B show that in a closed orientation, the left and right finger rings 107, 108 are adjacent or adjoining (see below), the curved tips 101, 102 of the first and second elongated elements 105, 104 contact each other, and the straight tips 114, 115 of the third and fourth elongated elements 110, 111 contact each other. In a closed orientation, the curved tip 102 of the first elongated element 104 contacts the curved tip 101 of the second elongated element 105, such that said contact between the first and second elongated elements is configured for securely holding a portion of towel, a portion of skin of the patient, or both. In use, the user inserts his fingers into the left and right finger rings 107, 108 to pull the rings together (towards each other), which results in the curved tips 101, 102 of the first and second elongated elements 105, 104 contacting each other and the straight tips 114, 115 of the third and fourth elongated elements 110, 111 contacting each other, which is the closed orientation.

FIGS. 2A-2B show that in a closed orientation, the curved tip 102 of the first elongated element and the curved tip 101 of the second elongated element are configured such that a gap 121 exists between a length 113 of the curved tip 102 of the first elongated element and a length 103 of the curved tip 101 of the second elongated element. Said gap is located between the distal end of the tips 101, 102 and the pivot point 134.

FIGS. 2A-2B show that in a closed orientation, length 133 of the straight tip 115 exists at the end of the third elongated element 110 and a length 132 of the straight tip 114 exists at the end of the fourth elongated element 111.

FIGS. 1A-1B show a first ratchet element 151 coupled to the right finger ring 108 adjacent to the first elongated element 104, as well as a second ratchet element 152 coupled to the left finger ring 107 adjacent to the second elongated element 105. FIGS. 1A-1B show that in the open orientation, the first and second ratchet elements 151, 152 are apart or separated. FIGS. 2A-2B show that in the closed orientation, the first and second ratchet elements 151, 152 are coupled together to secure the surgical towel clamp 100 in the closed orientation. FIGS. 1A-1B also show a third ratchet element 161 coupled to the right finger ring 108 adjacent to the third elongated element 110, as well as a fourth ratchet element 162 coupled to the left finger ring 107 adjacent to the fourth elongated element 105. FIGS. 1A-1B show that in the open orientation, the third and fourth ratchet elements 161, 162 are apart or separated. FIGS. 2A-2B show that in the closed orientation, the third and fourth ratchet elements 161, 162 are coupled together to secure the surgical towel clamp 100 in a closed orientation.

The surgical towel clamp 100 may be composed of any one of stainless steel, a metal alloy, plastic, or a plastic derivative. The surgical towel clamp 100 may be composed of a disposable material.

FIG. 3 is a perspective view of the surgical towel clamp 100 in use during an operation 300, in accordance with one embodiment. FIG. 3 shows that a surgical area 31 has been defined, which outlines the area in which a surgery will occur. A surgical area is a portion of the patient's body that will undergo a surgery and defines a point of entry of the surgeon and his tools for performing the surgery. FIG. 3 shows how the surgical towel clamp 100 may be used to secure towels or cloths (such as 305) for surgery. The surgical towels or cloths act as a barrier between the patient's skin and the surgical environment and provides a surface to wipe sterilized surgical instruments. The tips 101, 102 of the surgical towel clamp 100 are secured to the top portion 301 of the surgical towel of cloth 305, which works to keep the surgical cloth from moving excessively. The tips 101, 102 of the surgical towel clamp 100 may also be secured to a bight of skin under the portion 301, which works to keep the surgical area open. The tips 114, 115 of the surgical towel clamp 100 are secured to the bottom portion 302 of the surgical towel of cloth 305, which also works to keep the surgical cloth from moving excessively. The tips 114, 115 of the surgical towel clamp 100 may also be secured to a bight of skin under portion 302, which works to keep the surgical area open. This secures the surgical cloth to the surgical incision while opening the incision further so the surgeon may operate. The surgeon positions tips 101, 102 of the surgical towel clamp 100 over a bight of towel 301 and an underlying bight of the patient's skin and sets the towel clamp to grab the bight of towel 301 and the underlying bight of the patient's skin, such that the clamp is secured to the bight of towel 301 and a bight of skin using the ratchets. Then, the surgeon positions tips 114, 115 of the surgical towel clamp 100 over a bight of towel 302 and an underlying bight of the patient's skin and sets the towel clamp to grab the bight of towel 302 and the underlying bight of the patient's skin, such that the clamp is secured to the bight of towel 302 and a bight of skin using the ratchets. This further opens the incision and secures the surgical area by preventing receding of the towels or the patient's skin, should the surgeon be operating on a patient with taut skin.

Although specific embodiments of the claimed embodiments have been disclosed, those having ordinary skill in the art will understand that changes can be made to the specific embodiments without departing from the spirit and scope of the claimed embodiments. The scope of the claimed embodiments is not to be restricted, therefore, to the specific embodiments. Furthermore, it is intended that the appended claims cover any and all such applications, modifications, and embodiments within the scope of the claimed embodiments.

Embodiments herein, for example, are described above with reference to block diagrams and/or operational illustrations of methods and systems, according to said embodiments. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments have been described, other embodiments may exist. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A surgical towel clamp apparatus, comprising:
a first elongated element having a curved tip at a distal end, and a right finger ring at a proximal end;
a second elongated element having a curved tip at a distal end, and a left finger ring at a proximal end, wherein the first and second elongated elements are coupled at a first pivot point located between the distal and proximal ends of the first and second elongated elements;
a third elongated element having a straight tip at a distal end, and coupled to the right finger ring at a proximal end;
a fourth elongated element having a straight tip at a distal end, and coupled to the left finger ring at a proximal end, wherein the third and fourth elongated elements are coupled at a second pivot point located between the distal and proximal ends of the third and fourth elongated elements;
wherein in an open orientation, the left and right finger rings are apart, the curved tip of the first elongated element is apart from the curved tip of the second elongated element; and the straight tip of the third elongated element is apart from the straight tip of the fourth elongated element;
wherein in a closed orientation, the left and right finger rings are adjacent, the straight tip of the third elongated element contacts the straight tip of the fourth elongated element, and the curved tip of the first elongated element contacts the curved tip of the second elongated element, such that said contact between the first and second elongated elements is configured for securely holding a portion of towel, such that said contact between the first and second elongated elements is configured for securely holding a portion of skin, and such that a gap exists between a length of the curved tip of the first elongated element and a length of the curved tip of the second elongated element;
a first ratchet element coupled to the right finger ring adjacent to the first elongated element; and
a second ratchet element coupled to the left finger ring adjacent to the second elongated element;

wherein in the closed orientation, the first and second ratchet elements are coupled to secure the surgical towel clamp apparatus in a closed orientation.

2. The surgical towel clamp apparatus of claim 1, further comprising:
a third ratchet element coupled to the right finger ring adjacent to the third elongated element;
a fourth ratchet element coupled to the left finger ring adjacent to the fourth elongated element;
wherein in the closed orientation, the third and fourth ratchet elements are coupled to secure the surgical towel clamp apparatus in a closed orientation.

3. The surgical towel clamp apparatus of claim 2, wherein the right and left finger rings each comprise an oval shaped element for accommodating an individual's fingers.

4. The surgical towel clamp apparatus of claim 3, wherein the first pivot point is located at approximately a midpoint of the first and second elongated elements and wherein the second pivot point is located at approximately a midpoint of the third and fourth elongated elements.

5. The surgical towel clamp apparatus of claim 4, wherein the apparatus is composed of any one of stainless steel, a metal alloy, plastic, or a plastic derivative.

6. The surgical towel clamp apparatus of claim 5, wherein the apparatus is composed of a disposable material.

7. A surgical towel clamp apparatus, comprising:
a first elongated element having a curved tip at a distal end, and a right finger ring at a proximal end;
a second elongated element having a curved tip at a distal end, and a left finger ring at a proximal end, wherein the first and second elongated elements are coupled at a first pivot point located between the distal and proximal ends of the first and second elongated elements, and wherein the curved tips of the first and second elongated elements point in a first direction;
a third elongated element having a straight tip at a distal end, and coupled to the right finger ring at a proximal end;
a fourth elongated element having a straight tip at a distal end, and coupled to the left finger ring at a proximal end, wherein the third and fourth elongated elements are coupled at a second pivot point located between the distal and proximal ends of the third and fourth elongated elements, and wherein the straight tips of the third and fourth elongated elements point in a second direction opposite the first direction;
wherein in an open orientation, the left and right finger rings are apart, the curved tip of the first elongated element is apart from the curved tip of the second elongated element; and the straight tip of the third elongated element is apart from the straight tip of the fourth elongated element; and
wherein in a closed orientation, the left and right finger rings are adjacent, the straight tip of the third elongated element contacts the straight tip of the fourth elongated element, the curved tip of the first elongated element contacts the curved tip of the second elongated element, such that said contact between the first and second elongated elements is configured for securely holding a portion of towel, such that said contact between the first and second elongated elements is configured for securely holding a portion of skin, and such that a gap exists between a length of the curved tip of the first elongated element and a length of the curved tip of the second elongated element;
a first ratchet element coupled to the right finger ring adjacent to the first elongated element; and
a second ratchet element coupled to the left finger ring adjacent to the second elongated element;
wherein in the closed orientation, the first and second ratchet elements are coupled to secure the surgical towel clamp apparatus in a closed orientation.

8. The surgical towel clamp apparatus of claim 7, further comprising:
a third ratchet element coupled to the right finger ring adjacent to the third elongated element;
a fourth ratchet element coupled to the left finger ring adjacent to the fourth elongated element;
wherein in the closed orientation, the third and fourth ratchet elements are coupled to secure the surgical towel clamp apparatus in a closed orientation.

9. The surgical towel clamp apparatus of claim 8, wherein the right and left finger rings each comprise an oval shaped element for accommodating an individual's fingers.

10. The surgical towel clamp apparatus of claim 9, wherein the first pivot point is located at approximately a midpoint of the first and second elongated elements and wherein the second pivot point is located at approximately a midpoint of the third and fourth elongated elements.

11. The surgical towel clamp apparatus of claim 10, wherein the apparatus is composed of any one of stainless steel, a metal alloy, plastic, or a plastic derivative.

12. The surgical towel clamp apparatus of claim 11, wherein the apparatus is composed of a disposable material.

* * * * *